United States Patent
Färber et al.

(10) Patent No.: US 6,384,042 B2
(45) Date of Patent: May 7, 2002

(54) SYSTEMIC USE OF 5-HT3 RECEPTOR ANTAGONISTS AGAINST RHEUMATIC INFLAMMATORY PROCESSES

(76) Inventors: Lothar Färber, Drosselweg 6, 90562 Heroldsberg (DE); Wolfgang Müller, Im Rehwechsel 30, 4102 Binningen (CH); Thomas Stratz, Purkersdorferstrasse 49, 79713 Bad Säckingen (DE)

( * ) Notice: Subject to any disclaimer, the term of this patent is extended or adjusted under 35 U.S.C. 154(b) by 0 days.

(21) Appl. No.: 09/931,679

(22) Filed: Aug. 16, 2001

Related U.S. Application Data

(63) Continuation of application No. PCT/EP00/01268, filed on Feb. 16, 2000.

(30) Foreign Application Priority Data

| Feb. 18, 1999 | (GB) | 9903755 |
| Jun. 25, 1999 | (GB) | 9914947 |

(51) Int. Cl.$^7$ ...................... A61K 31/44; A61K 31/415
(52) U.S. Cl. ...................... 514/278; 514/397
(58) Field of Search ................. 514/278, 397

(56) References Cited

U.S. PATENT DOCUMENTS 5,006,330 A * 4/1991 Sternberg et al.

FOREIGN PATENT DOCUMENTS

| EP | 0 189 002 | 7/1986 |
| GB | 1111733 | * 5/1968 |
| WO | WO 93/17019 | 9/1993 |
| WO | WO 95/27490 | 10/1995 |
| WO | WO 95/30423 | 11/1995 |
| WO | WO 97/36586 | 10/1997 |

OTHER PUBLICATIONS

Misztal et al., 5–HT3 serotonin receptors, Database–Caplus, AN1998:193478, abstract, Wiad. Chem., 1997, vol. 50(9–10), 623–641.*

Devlin et al., Granisetron suppresses methotrexate . . . , Database–Caplus, AN 1999:252929, abstract, Rheumatology, 1999, vol. 38/3, pp. 208–282.*

Sternberg et al., Inflammatory mediator–induced hypothalamic . . . , Database–Caplus, AN 1989:210290, abstract, Proc. natl. Acad. Sci. 1989, 86/7, pp. 2374–2378.*

Blanco et al., "Ondansetron Therapy is Useful in Refractory and Severe Methotrexate–Induced Nausea in Rheumatoid Arthritis," Abstract XP–000886199, British Journal of Rheumatology, vol. 37, p. 117 (1998).

Cunningham et al., "Optimum Anti–emetic Therapy for Cisplatin Induced Emisis Over Repeat Courses: Ondansetron Plus Dexamethasone Compared with Metoclopramide, Dexamethasone Plus Lorazepam," XP–000886538, Annal of Oncology, vol. 7, pp. 277–282 (1996).

Devlin et al., "Granisetron (Kytril) Suppresses Methotrexate–induced Nausea and Vomiting Among Patients with Inflammatory Arthritis and is Superior to Prochlorperazine (Stemetril)," Rheumatology, vol. 38, pp. 280–282 (1999).

Doak et al., "Formalin–Induced Nociceptive Behavior and Edema: Involvement of Multiple Peripheral 5–hydroxytryptamine Receptor Subtypes," XP–000886556, Neuroscience, vol. 80, No. 3, pp. 939–949 (1997).

Giordano et al., "Peripherally Administered Serotonin 5–HT$_3$ Receptor Antagonists Reduce Inflammatory Pain in Rats," European Journal of Pharmacology, vol. 170, pp. 83–86 (1989).

Rosenstein et al., "Antinociceptive Effects of Microdialysis Administration of 5–HT$_{1A}$ and 5–HT$_3$ Receptor Agonists and Antagonists in a Model of Acute Arthritis," Abstract XP–000886228, Society for Neuroscience Abstracts, vol. 23, p. 1540 (1997).

* cited by examiner

*Primary Examiner*—William R. A. Jarvis
*Assistant Examiner*—Vicki Kim
(74) *Attorney, Agent, or Firm*—Carol A. Loeschorn

(57) ABSTRACT

The present invention relates to a new use for compounds having 5-HT$_3$ (serotonin M) receptor antagonist activity, especially tropisetron, for the manufacture of a pharmaceutical composition for the systemic treatment of an inflammatory rheumatic or rheumatoid disease other than crystal induced arthritis and other than living pathogen induced inflammatory diseases as long as the living pathogen is still present.

10 Claims, No Drawings

SYSTEMIC USE OF 5-HT3 RECEPTOR ANTAGONISTS AGAINST RHEUMATIC INFLAMMATORY PROCESSES

This application is a continuation of PCT Patent Application No. PCT/EP00/01268, filed Feb. 16, 2000, which is herein incorporated by reference.

The present invention relates to a new use, in particular a new pharmaceutical use for compounds having 5-HT$_3$ (serotonin M) receptor, in particular specific 5-HT$_3$ receptor, antagonist activity, especially in the manufacture of a pharmaceutical composition.

The 5-HT$_3$-receptor antagonists comprise a defined and recognised class of pharmaceutically active compounds well known in the art and characterised, as their name implies, by their pharmacological activity. Various 5-HT$_3$ receptor antagonist compounds are commercially available and clinically applied, e.g. in the treatment of emesis.

In accordance with the present invention it has now surprisingly been found that 5-HT$_3$ receptor antagonists are useful for the systemic treatment of inflammatory rheumatic or rheumatoid diseases other than crystal induced arthritis, especially gout, and from living pathogen induced inflammatory diseases as long as the living pathogen is still present, especially of inflammation, e.g. of inflammatory processes, conditions, events and disease as well as their sequelae or symptoms, associated with rheumatic or rheumatoid diseases.

Hence, the present invention relates to the use of a 5-HT$_3$ receptor antagonist or of a pharmaceutically acceptable salt of such an antagonist for the manufacture of a pharmaceutical composition for the systemic treatment of an inflammatory rheumatic or rheumatoid disease other than crystal induced arthritis and other than living pathogen induced inflammatory diseases as long as the living pathogen is still present, for example the treatment of any process, condition, event, or disease as hereinafter described. In particular, the present invention provides the use as mentioned before where, in addition to pain, at least one further sequela or symptom in addition to pain that is associated with the inflammatory rheumatoid or rheumatic disease is alleviated, ameliorated or controlled.

Any 5-HT$_3$ receptor antagonist can be used in accordance with the invention. Preferred 5-HT$_3$ receptor antagonists which may be employed in accordance with the present invention are:

A) Ondansetron [1,2,3,9-tetrahydro-9-methyl-3-[(2-methyl-IH-imidazol-1-yl]methyl]-4H-carbazol-4-one (cf. Merck Index, twelfth edition, item 6979);

B) Granisetron [endo-1-methyl-N-(9-methyl-9-aza-bicyclo[3.3.1]non-3-yl)-IH-imidazole-3-carboxamide: (cf. loc. cit., item 4557); and C) Dolasetron [IH-indole-3-carboxylic acid (2α, 6α, 8α, 9αβ)-octahydro-3-oxo-2,6-methano-2H-quinolizin-8-yl ester] (cf. loc. cit., item 3471).

Particular 5-HT$_3$ receptor antagonists which may be employed in accordance with the present invention are those of the formula 1 as defined in European Patent Publication 189002 B1, the contents of which are incorporated herein by reference, in particular the compound:

D) Indol-3-yl-carboxylic acid-endo-8-methyl-8-aza-bicyclo[3,2,1]-oct-3-yl-ester, also known as tropisetron. (cf. loc.cit., item 9914).

Further 5-HT$_3$ receptor antagonists which may be used preferably in accordance with the present invention are:

E) 4,5,6,7-tetrahydro-5-[(1-methyl-indol-3-yl)carbonyl] benzimidazole (see also ramosetron, see U.S. Pat. No. 5,344,927);

F) (+)-10-methyl-7-(5-methyl-1H-imidazol-4-ylmethyl)-6,7,8,9-tetrahydropyrido[1,2-a]indol-6-one (see also fabesetron, EP 0 361 317); and G) [N-(1-ethyl-2-imidazolin-2-yl-methyl)-2-methoxy-4-amino-5-chlorobenzamide (see also lintopride-Chem.-Abstr.-No. 107429-63-0).

A further 5-HT$_3$ receptor antagonists which may be used preferably in accordance with the present invention is H) 2,3,4,5-tetrahydro-5-methyl-2-[(5-methyl-1H-imidazol-4-yl)methyl]-1H-pyrido[4,3-b]indol-1-one (see also alosetron, EP 0 306 323).

Each of these compounds, alone or in combination with one or more other 5-HT$_3$ inhibitor, may be used for the treatment according to the invention.

For use in accordance with the present invention tropisteron (especially in the formulation called NAVOBAN®) is most preferred.

5-HT$_3$-receptor antagonists may be employed in accordance with the invention in free or in pharmaceutically acceptable salt form, e.g. as known in the art, for example, in the case of compounds A) to D) above in pharmaceutically acceptable acid addition salt form, for example, in the case of: compound A) the hydrochloride dihydrate; compound B) the hydrochloride; compound C) the mesylate; and compound D) the monohydrochloride. References to 5-HT$_3$ receptor antagonists collectively or individually throughout the present specification and claims are accordingly to be understood as embracing both free compounds and such pharmaceutically acceptable salt forms, e.g. as clinically employed, and further also solvates, e.g. hydrates, or specific crystal forms of any of these compounds or salts.

Thus, the invention relates to the use of a 5-HT$_3$ receptor antagonist or of a pharmaceutically acceptable salt of such an antagonist for the manufacture of a pharmaceutical composition for the systemic treatment of an inflammatory rheumatic or rheumatoid disease other than crystal induced arthritis and other than living pathogen induced inflammatory diseases as long as the living pathogen is still present, where the 5-HT$_3$ receptor antagonist is selected from the group consisting of ondansetron, granisetron, dolasetron, tropisetron, ramosetron, fabesetron, lintopride and alosetron, which may be used in free form, that is, not as a salt, or as a pharmaceutically acceptable salt.

In accordance with the present invention it has now surprisingly been found that 5-HT$_3$ receptor antagonists are useful for the treatment of inflammation. They are useful for the treatment of inflammatory rheumatic or rheumatoid processes, conditions or events, for example, consequential to disease (including infection, for example viral infection, with the proviso that in case of an acute infection or parasite infestation, e.g. bacterial, fungal or, in a broader sense, viral or protozoal infection, or infestation by a parasite, first treatment of the infection or infestation itself, e.g. with antibiotics or other treatment, is indicated to remove the living pathogen before the 5-HT$_3$ antagonist is used), as well for the treatment of inflammatory disease as such.

"Treatment" as used herein includes systemic use for the alleviation, amelioration or control of inflammation, e.g. of inflammatory rheumatic or rheumatoid disease, process, condition or event. It also includes intervention for the alleviation, amelioration or control of the sequelae or symptoms of inflammation, for example degeneration (e.g. of cells, epithelia or tissues), or especially swelling, exudation or effusion, or pain. In this context the term "treatment" is further to be understood as embracing use to reverse, restrict or control progression of any specified disease, process, condition, event or the like, including use for disease modifying effect. If any of the mentioned diseases, processes, conditions or events is associated with pain, the term "treatment" preferably encompasses the alleviation, amelioration or control (including temporal or permanent removal) of at least one further sequela or symptom in addition to pain, such as swelling, effusion, exsudation, stiffness, lack of flexibility of joints, or degeneration, more preferably of all symptoms and most preferably of the total clinical picture of the respective disease, irritation or manifestation.

The present invention is in particular applicable to the systemic treatment of an inflammatory disease other than crystal induced arthritis (gout) or preferably other than living pathogen induced inflammation as long as the living pathogen is still present, especially of manifestations at the locomotor apparatus, such as various inflammatory rheumatoid diseases (except for crystal induced arthritis (e.g. gout) and living pathogen induced diseases as long as the pathogen (e.g. a virus, bacterium, fungus, protozoon or parasite) is still present, so that causal treatment against the pathogen is indicated first, such as (1) chronic polyarthritis (=rheumatoid arthritis), including juvenile arthritis or psoriasis arthropathy;
(2) paraneoplastic syndrome or tumor-induced inflammatory diseases,
(3) turbid effusions,
(4) collagenosis, such as systemic Lupus erythematosus, poly-myositis, dermato-myositis, systemic sclerodermia or mixed collagenosis;
(5) postinfectious arthritis (where no living pathogenic organism can be found at or in the affected part of the body), or
(6) seronegative spondylarthritis, such as spondylitis ankylosans;

or further
(7) vasculitis,
(8) sarcoidosis, or
(9) arthrosis;

or further any combinations thereof.

An example of a preferred inflammation to be treated systemically is
a) synovial inflammation, for example, synovitis, including any of the particular forms of synovitis recited in Dorland's Illustrated Medical Dictionary, 26th edition, pub. W. B. Saunders and Co. at page 1301, in particular bursal synovitis and purulent synovitis, as far as it is not crystal-induced. Such synovial inflammation may for example, be consequential to or associated with disease, e.g. arthrosis, including arthritis, e.g. osteoarthritis, rheumatoid arthritis or arthritis deformans.

The present invention is further applicable to the systemic treatment of:
b) Inflammation, e.g. inflammatory diseases or conditions, of the joints or locomotor apparatus in the region of the tendon insertions and tendon sheaths.

Such inflammation may, for example, be consequential to or associated with disease or further (in a broader sense of the invention) with surgical intervention, e.g. as recited under a) above, including, in particular conditions such as insertion endopathy, myofasciale syndrome and tendomyosis.

The present invention is especially applicable to the treatment of:
c) Inflammation, e.g. inflammatory disease or condition, of connective tissues.

Such diseases or conditions include in particular dermatomyositis and myositis.

From the foregoing it will be understood that the present invention is to be further understood as embracing the systemic treatment, e.g. therapy, of any disease or condition as set forth above, for example arthrosis, dermatomyositis etc., for example, for the alleviation or control of inflammatory processes or events and their sequelae associated therewith or consequential thereto, e.g. for the treatment of rheumatoid arthritis, e.g. to alleviate or control joint inflammation or effusion.

In the case of the inflammatory diseases, diseases where a living pathogen, e.g. a virus, a bacterium, a fungus, a protozoon or a parasite or the like, is still present, the treatment of must first aim at removal of the pathogen causative for the disease, before treatment with a 5-HT$_3$ antagonist is used, as otherwise there is the danger that the causative pathogen remains intact. Then the mere symptomatic treatment with a 5-HT$_3$ antagonist is contraindicated in order to avoid survival or even further spread of the causative infection. This is also valid in the case of combination with an anti-inflammatory glucocorticosteroid as described in the following, as is the proviso that treatment of crystal-induced inflammation is excluded.

In a further aspect it has been found in accordance with the present invention that systemic administration of 5-HT$_3$ receptor antagonists is useful as replacement therapy for anti-inflammatory glucocorticosteroid, e.g. cortisone or the like, therapy. For example for use in any means of treatment as hereinbefore set forth.

The term "replacement therapy" as used herein is to be understood as embracing both use "as full replacement", i.e. use instead of anti-inflammatory glucocorticosteroid therapy, as well as use "as partial replacement" for anti-inflammatory glucocorticosteroid therapy, i.e. for administration together with anti-inflammatory glucocorticosteroid therapy or as a means of reducing glucocorticosteroid dosage or to achieve a glucocorticosteroid sparing effect.

The present invention accordingly provides:

I. A method of treating inflammation, for example treating any process, condition, event, or disease as hereinbefore set forth, in a subject in need thereof, which method comprises administering systemically an effective amount of a 5-HT$_3$ receptor antagonist;

II. A method of providing replacement therapy for anti-inflammatory glucocorticosteroid therapy in a subject receiving such glucocorticosteroid therapy, for example for or in the treatment of any process, condition, event or disease as hereinbefore set forth, which process comprises systemicalls administering to said subject an effective amount, e.g. an anti-inflammatory glucocorticosteroid sparing amount, of a 5-HT$_3$-receptor antagonist; as well as III. A method of treating inflammation, for example treating any process, condition, event or disease as hereinbefore set forth, in a subject in need thereof, which method comprises systemically administering an effective amount of a 5-HT$_3$ receptor antagonist together with an anti-inflammatory glucocorticosteroid.

Where co-administration is practiced as under III above the drug substances, i.e. 5-HT$_3$ receptor antagonist and anti-inflammatory glucocorticosteroid may be administered sequentially or simultaneously or substantially simultaneously, e.g. employing a fixed combination dosage form.

In further aspects the present invention also provides:

IV. A 5-HT$_3$ receptor antagonist for use in, or for use in the manufacture of a pharmaceutical composition for use in; or the use of a pharmaceutical composition comprising a 5-HT$_3$ receptor antagonist for systemic use:

a) in the treatment of inflammation, for example any inflammatory process, condition, event or disease as hereinbefore set forth;
b) as replacement therapy for anti-inflammatory glucocorticosteroid therapy, for example in the treatment of any inflammatory process, condition, event or disease as hereinbefore set forth; or
c) for co-administration together with an anti-inflammatory glucocorticosteroid in the treatment of inflammation, for example in the treatment of any inflammatory process, condition, event or disease as hereinbefore set forth; as well as V. A pharmaceutical dosage form for systemic administration comprising a 5-HT$_3$ receptor antagonist together with an anti-inflammatory glucocorticosteroid.

The terms "systemically administering" or "systemic use" refer to a way of administration that is not local (=at or near the site of a disease manifestation), but that leads to exposure of most or all of the parts of the body to the 5-HT$_3$-antagonist.

Dosage forms in accordance with V above are to be understood as including both fixed-unit-dosage forms, e.g. tablets, capsules, liquid formulations and the like comprising both active ingredients together with appropriate pharmaceutically acceptable diluents or carriers, as well as twin delivery systems, packages or the like comprising both active ingredients separately or in separate dosage form, for concommitant or sequential administration.

Utility of 5-HT$_3$ receptor antagonists in accordance with the present invention can be demonstrated in clinical trials carried in accordance with standard techniques and methodologies, for example as follows:

The following examples are for illustrative purposes and are not intended to diminish the scope of the present invention. Instead of tropisetron, any other 5-HT$_3$-antagonist, or a pharmaceutically acceptable salt thereof, solvate, e.g. hydrate, or crystalline form thereof, especially selected from the group consisting of ondansetron, granisetron, dolasetron, ramosetron, fabesetron, lintopride and alosetron, can be used, or any combination of two or more of these 5-HT$_3$ receptor antagonists or pharmaceutically acceptable salts thereof.

EXAMPLE 1

Treatment of Synovial Inflammation/synovitis Consequent to Inflammatory Processes Trials are performed on a patient exhibiting rheumatoid arthritis and severe consequential synovial inflammation as well as marked pain.

The patient had previously been treated, largely unsuccessfully, with methotrexate, azathioprin and cyclosporin and at entry into the trial exhibits severe synovial swelling in particular of the finger joints, the wrist and in the knee joint (accompanied by effusion or exudation). The subject is treated for 5 days sequentially with tropisetron administered at a dose of 2 mg/day i.v. Treatment results in amelioration of the synovial inflammation, a reduction of stiffness in the morning and remission from the formation of effusion in the kneejoint. There is a reduction of the measure parameters for inflammation as well as a marked reduction of glucocorticoid requirements.

EXAMPLE 2

Treatment of Synovial Inflammation

A patient exhibits damage to the meniscus of the right knee joint as well as arthritic change leading to synovial inflammation with consequential knee joint effusion. Despite a successful synovialectomy prior to trial entry the patient exhibits renewed knee joint effusion. Two 2 mg doses of tropisetron are administered i.v. over a period of 17 days with 15 injections, one each day with a 2 days pause in therapy. 24 hours after the first i.v. injection, significant improvement of pain is reported. Following continuation of injections, the patient exhibits as virtually free of symptoms. The exudation from the knee joint is completely inhibited without any other medication within 8 days and movement of the knee joint is clearly improved. The improvement in condition continues over a further 7 days observation following completion of therapy.

EXAMPLE 3

Treatment of Dermatomyositis/vasculitis

A patient exhibiting marked dermatomyositis with accompanying bioptically verified vasculitis receives 3 injections i.v., each of 2 mg tropisetron. Virtually complete remission of the massive reddening of the skin and a clear reduction of pain symptoms is observed, already after the first injection. The patient remains substantially complaint free over a period of one week following indicating effective control of inflammatory event.

Equivalent results are obtainable in equivalent or comparable trials with patients exhibiting similar symptomatology employing 5-HT$_3$-receptor antagonists other than tropisetron, for example using any of the 5-HT$_3$-receptor antagonists A) through C) or E) through H) hereinbefore recited at comparable, e.g. conventional clinical, dose as known in the art. Similar results are also achievable employing 5-HT$_3$-receptor antagonists, e.g. tropisetron at doses of the order of 2 mg/day p.o. or by injection or topical application in clinical trials involving subjects exhibiting other inflammatory diseases, conditions or symptoms as herein specified.

Trials conducted as described above or analogously are demonstrative of long lasting and disease modifying effects in conditions herein described as well as symptomatic and antiinflammatory glucocorticosteroid replacement effect for 5-HT$_3$ receptor antagonists.

For use in accordance with the present invention the appropriate dosage will, of course, vary depending on for example the particular 5-HT$_3$ receptor antagonist employed the mode of administration and the nature and severity of the condition to be treated as well as the specific condition to be treated. In general an indicated daily dosage will be in the range usually employed for known indications such as emesis and will typically be from about 0.05 to about 50 mg per day conveniently administered once or in divided doses up to four times a day or in sustained release form. In the case of tropisetron an appropriate dosage for administration, e.g. by injection, for example for i.v. application or injection direct into the tissues, will be of the order of 2 mg or up to and including 5 mg per day, administered once, sequentially over a sequence of 2 to 20 days or at intervals of 2 to 5 days to 2 days to 2 weeks.

For use in accordance with the invention, 5-HT$_3$ receptor antagonists may be administered systemically by any conventional route in particular enterally, preferably orally, e.g. in the form of tablets or capsules, or via suppositories or or most preferably parenterally, e.g. in the form of injectible solutions or suspensions, for intravenous, intra-muscular (not for local but for systemic treatment), sub-cutaneous (not for local but for systemic treatment) or intra-peritoneal administration, or for infusion. In the case of intravenous administration bolus injection is preferred. Suitable formulations for use in accordance with the present invention will include any of those as known and commercially available and employed in clinic in the art. By systemically administration, it is meant that the administration is not at or near the site of a disease manifestation with the goal to reach a higher local concentration of the administered 5-$HT_3$ receptor antagonist at that site (though it may not be possible to avoid this, e.g. where the whole body is affected), but aims at systemic exposure of most of or all of the body, generally also including the site of administration.

What is claimed is:

1. A method for systemic treatment of an inflammatory rheumatic or rheumatoid disease or condition, other than crystal induced arthritis and other than living pathogen induced inflammatory diseases, as long as the living pathogen is still present comprising administering a therapeutically effective amount of a 5-$HT_3$ receptor antagonist or a pharmaceutically acceptable salt thereof to a subject in need thereof, wherein the disease to be treated is selected from the group consisting of:
   (1) chronic polyarthritis,
   (2) paraneoplastic syndrome or tumor-induced inflammatory diseases,
   (3) turbid effusions,
   (4) collagenosis,
   (5) postinfectious arthritis,
   (6) seronegative spondylarthritis,
   (7) vasculitis,
   (8) sarcoidosis, and
   (9) arthrosis.

2. A method for systemic treatment of an inflammatory rheumatic or rheumatoid disease or condition, other than crystal induced arthritis and other than living pathogen induced inflammatory diseases, as long as the living pathogen is still present comprising administering a therapeutically effective amount of a 5-$HT_3$ receptor antagonist or a pharmaceutically acceptable salt thereof to a subject in need thereof, wherein the 5-$HT_3$ receptor antagonist is selected form the group consisting of ondansetron, granisetron, dolasetron, tropisetron, ramosetron, fabesetron, lintopride and alosetron or pharmaceutically acceptable salts thereof.

3. A method according to claim 1 where, in addition to pain, at least one further sequela or symptom that is associated with the inflammatory rheumatoid or rheumatic disease or condition is alleviated, ameliorated or controlled.

4. A method according to claim 1 wherein the 5-$HT_3$ receptor antagonist is selected from the group consisting of ondansetron, granisetron, dolasetron, tropisetron, ramosetron, fabesetron, lintopride and alosetron or pharmaceutically acceptable salts thereof.

5. A method according to claim 2, wherein the disease to be treated is a disease other than crystal induced arthritis and is selected from the group consisting of:
   (1) chronic polyarthritis,
   (2) paraneoplastic syndrome or tumor-induced inflammatory diseases,
   (3) turbid effusions,
   (4) collagenosis,
   (5) postinfectious arthritis,
   (6) seronegative spondylarthritis,
   (7) vasculitis,
   (8) sarcoidosis, and
   (9) arthrosis.

6. A method according to claim 1, wherein the disease to be treated is a disease other than crystal induced arthritis and is selected from the group consisting of:
   (1) chronic polyarthritis,
   (2) paraneoplastic syndrome or tumor-induced inflammatory diseases,
   (3) turbid effusions,
   (4) collagenosis,
   (5) postinfectious arthritis, and
   (6) seronegative spondylarthritis.

7. A method of systemically treating an inflammatory rheumatic or rheumatoid disease or condition other than crystal induced arthritis and other than living pathogen induced inflammatory diseases as long as the living pathogen is still present in a subject in need thereof, which method comprises administering to said subject a therapeutically effective amount of a 5-$HT_3$ receptor antagonist or pharmaceutically acceptable salts thereof and an anti-inflammatory glucocorticosteroid.

8. A method according to claim 1 wherein the 5-$HT_3$ receptor antagonist is tropisetron or a pharmaceutically acceptable salt thereof.

9. A method according to claim 8 where, in addition to pain, at least one further sequela or symptom that is associated with the inflammatory rheumatoid or rheumatic disease or condition is alleviated, ameliorated or controlled.

10. A method according to claim 8 wherein the 5-$HT_3$ receptor antagonist is tropisetron or a pharmaceutically acceptable salt thereof.

* * * * *

UNITED STATES PATENT AND TRADEMARK OFFICE
CERTIFICATE OF CORRECTION

PATENT NO. : 6,384,042 B2
DATED : May 7, 2002
INVENTOR(S) : Lothar Farber et al.

It is certified that error appears in the above-identified patent and that said Letters Patent is hereby corrected as shown below:

Column 6,
Line 64, should read -- in the form of tablets or capsules, or via suppositories or --

Column 7,
Line 43, should read -- from the group consisting of ondansetron, granisetron --

Column 8,
Line 43, should read -- A method according to claim 2 wherein, in addition to --
Line 47, should read -- A method according to claim 2 wherein the $5\text{-}HT_3$ --

Signed and Sealed this

Third Day of December, 2002

JAMES E. ROGAN
*Director of the United States Patent and Trademark Office*